US00PP28837P3

(12) United States Plant Patent
Meinl

(10) Patent No.: US PP28,837 P3
(45) Date of Patent: Jan. 2, 2018

(54) ***HYDRANGEA* PLANT NAMED 'SAXBRIWHI'**

(50) Latin Name: *Hydrangea macrophylla*
Varietal Denomination: SAXBRIWHI

(71) Applicant: Kühne Jungpflanzen Claus Kühne, Dresden (DE)

(72) Inventor: Katrin Meinl, Dresden (DE)

(73) Assignee: Kühne Jungpflanzen Claus Kühne, Dresden (DE)

( * ) Notice: Subject to any disclaimer, the term of this patent is extended or adjusted under 35 U.S.C. 154(b) by 13 days.

(21) Appl. No.: 14/999,310

(22) Filed: Apr. 22, 2016

(65) Prior Publication Data

US 2016/0374247 P1 Dec. 22, 2016

Related U.S. Application Data

(60) Provisional application No. 62/230,924, filed on Jun. 18, 2015.

(51) Int. Cl.
*A01H 5/02* (2006.01)

(52) U.S. Cl.
USPC ..... Plt./250

(58) Field of Classification Search
USPC ..... Plt./250
See application file for complete search history.

*Primary Examiner* — Keith O Robinson
(74) *Attorney, Agent, or Firm* — Audrey Charles

(57) ABSTRACT

A new and distinct cultivar of *Hydrangea* plant named 'SAXBRIWHI', characterized by its white-colored inflorescences, dark green-colored foliage, and moderately vigorous, upright growth habit, is disclosed.

1 Drawing Sheet

Latin name of genus and species of plant claimed: *Hydrangea macrophylla.*

Variety denomination: 'SAXBRIWHI'.

BACKGROUND OF THE INVENTION

The present invention relates to a new and distinct cultivar of *Hydrangea* plant botanically known as *Hydrangea macrophylla* and hereinafter referred to by the cultivar name 'SAXBRIWHI'.

The new cultivar originated in a controlled breeding program in Dresden, Germany during the early summer of 2006. The objective of the breeding program was the development of *Hydrangea* cultivars that have strong stems and long-lasting inflorescences.

The new *Hydrangea* cultivar is the result of cross-pollination. The female (seed) parent of the new cultivar is a proprietary *Hydrangea macrophylla* breeding selection coded A15-1, not patented, characterized by its lacecap-type, pink-colored inflorescences, large dark green-colored foliage, and highly vigorous, upright growth habit. The male (pollen) parent of the new cultivar is a proprietary *Hydrangea macrophylla* breeding selection coded 6-99/4, not patented, characterized by its mophead-type, white to slightly pink colored inflorescences, small dark green-colored foliage, and low growth vigor, compact-upright growth habit. The new cultivar was discovered and selected as a single flowering plant within the progeny of the above stated cross-pollination during April 2008 in a controlled environment in in Dresden, Germany.

Asexual reproduction of the new cultivar by softwood cuttings since June 2008 in Dresden, Germany has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'SAXBRIWHI' as a new and distinct cultivar of *Hydrangea* plant:

1. White-colored inflorescences;
2. Dark green-colored foliage; and
3. Moderately vigorous, upright growth habit.

Plants of the new cultivar differ from plants of the female and male parents primarily in growth vigor and inflorescence color.

Of the many commercially available *Hydrangea* cultivars, the most similar in comparison to the new cultivar is Tea Time 'Clarissa', not patented. However, in side-by-side comparison, plants of the new cultivar differ from plants of 'Clarissa' in at least the following characteristics:

1. Plants of the new cultivar have an inflorescence color that is purer white than plants of 'Clarissa';
2. Plants of the new cultivar have shallower leaf serration than plants of 'Clarissa'; and
3. Plants of the new cultivar have a faster rooting period than plants of 'Clarissa'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs may differ slightly from the color values cited in the detailed description, which accurately describes the colors of 'SAXBRIWHI'. The plants were grown in 13.0 cm containers for approximately ten months in Dresden, Germany. Detailed growing conditions are described in the following section.

DETAILED BOTANICAL DESCRIPTION

Figure 1:
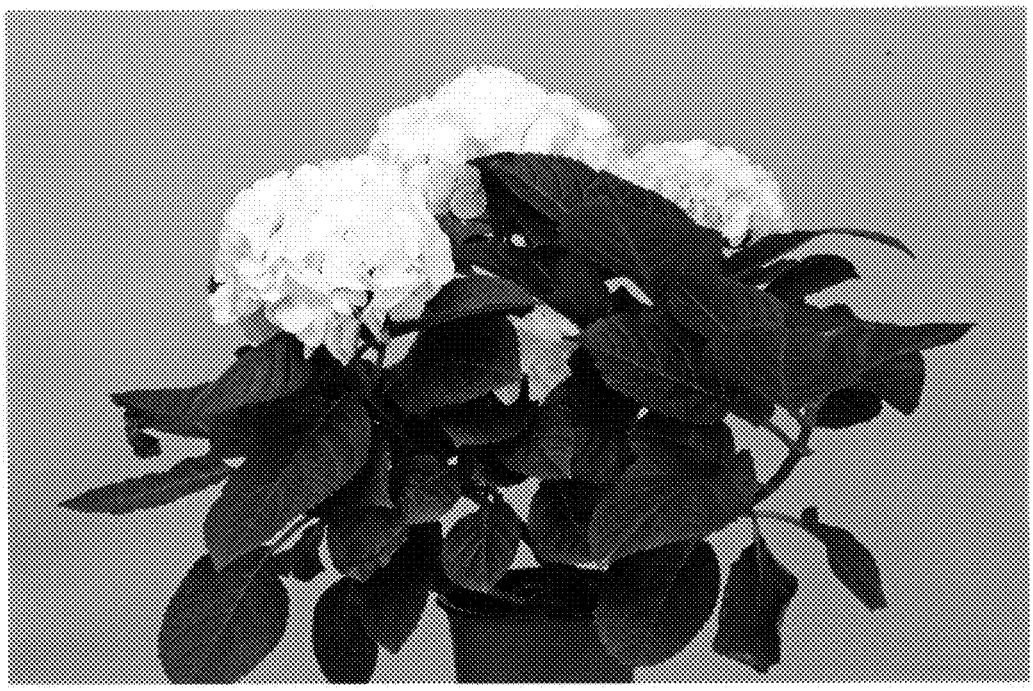
FIG. 1 illustrates a side view of the overall growth and flowering habit of 'SAXBRIWHI'.
Figure 2:
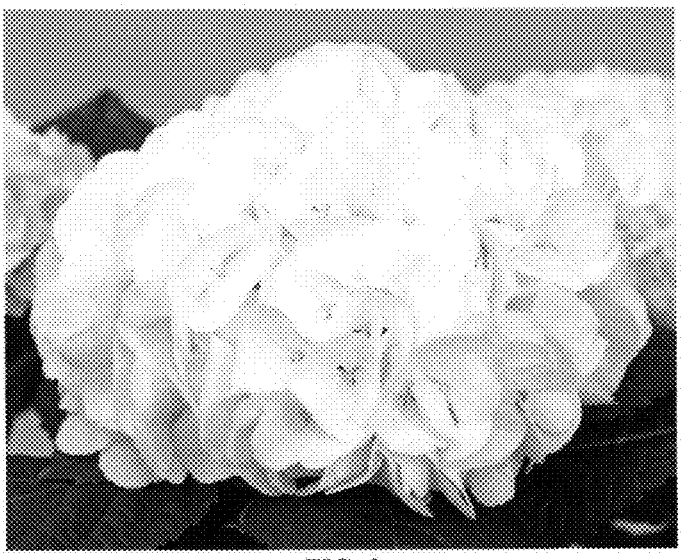
FIG. 2 illustrates a close-up view of an inflorescence of 'SAXBRIWHI'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The plant history was taken in February 2016 on plants grown in 13.0 cm containers for approximately ten months in Dresden, Germany. Plants were grown outside and then forced to flowering in a greenhouse for an 11 week period. During the forcing period greenhouse temperatures ranged from 64° F. to 75° F. (18° C. to 24° C.) with 3,500 klx/qm supplemental lighting. Plants were treated five times with 0.3% of the growth regulator Dazide, two times during outside cultivation and three times during the forcing period. Plants were pinched twice, five weeks after sticking the unrooted cutting, and then six weeks after transplant to the 13 cm pot. Observations were made when the plants were in natural daylight conditions in Boskoop, The Netherlands. Measurements and numerical values represent averages of typical plants.

Botanical classification: *Hydrangea macrophylla* 'SAXBRIWHI'.

Parentage:

*Female parent.*—Proprietary *Hydrangea macrophylla* breeding selection coded A15-1, not patented.

*Male parent.*—Proprietary *Hydrangea macrophylla* breeding selection coded 6-99/4, not patented.

Propagation:

*Type cutting.*—Terminal stem cuttings.

*Time to initiate roots during the summer.*—Approximately 16 days.

*Time to produce a rooted cutting during the summer.*—Approximately 28 days.

*Time to initiate roots during the winter.*—Approximately 18 days.

*Time to produce a rooted cutting during the winter.*—Approximately 31 days.

*Root description.*—Medium thickness, fibrous.

*Rooting habit.*—Moderate branching and density.

Plant description:

*Commercial crop time.*—Approximately 30 to 34 weeks of cultivation from a rooted cutting followed by 9 to 11 weeks of forcing to finish in a 13.0 cm pot.

*Growth habit and general appearance.*—Deciduous shrub, mophead-type *Hydrangea.* Moderately vigorous, upright.

*Hardiness.*—USDA Zone 5a (−20° F. to −15° F.).

*Heat tolerance.*—Regularly tolerates temperatures as high as 38° C. in the summer.

*Size.*—Height from soil level to top of plant plane: Approximately 29.8 cm. Width: Approximately 48.6 cm.

*Branching habit.*—Moderately freely branching. Pinching enhances branching. Quantity of lateral branches per plant: Approximately 7.

*Branch.*—Shape: Rounded. Strength: Strong. Fasciation: Absent. Length to base of inflorescence: Approximately 17.7 cm. Diameter: Approximately 6.0 mm. Length of central internode: Approximately 2.2 cm. Texture of young stem: Glabrous. Texture of mature stem: Woody. Color of young stem: 143A. Color of mature stem: 200A to 200B.

*Lenticels.*—Quantity per internode: Approximately 18. Shape: Round to elliptic, positioned vertically. Size: Approximately 0.5 mm to 1.5 mm. Color: 187A.

Foliage description:

*General description.*—Quantity of leaves per lateral branch: Approximately 12. Fragrance: None detected. Form: Simple. Arrangement: Opposite.

*Leaves.*—Aspect: Flat. Shape: Ovate to near elliptic. Margin: Serrated. Apex: Acute. Base: Short attenuate. Venation pattern: Pinnate. Length of mature leaf: Approximately 12.5 cm. Width of mature leaf: Approximately 8.8 cm. Texture of upper and lower surfaces: Moderately rugose, glabrous. Variegation: Absent. Color of upper surface of young foliage: 144A with venation of 144A. Color of lower surface of young foliage: 144A with venation of 144A. Color of upper surface of mature foliage: Closest to but more yellow than NN137A with venation of 143B. Color of lower surface of mature foliage: 137B with venation of 143C.

*Petiole.*—Length: Approximately 2.9 cm. Diameter: Approximately 4.0 mm. Texture: Glabrous. Color: 144A to 144B.

Flowering description:

*Flowering habit.*—Seasonal, May through August.

*Lastingness of individual inflorescence on the plant.*—Approximately 1.5 months.

Inflorescence description:

*General description.*—Type: Terminal globular, single-type, mophead, compound corymb of fertile florets and rotate-shaped, sterile, sepalous florets borne on the same corymb, persistent. Sterile florets occasionally have visible reproductive parts. Quantity per plant: Approximately 4. Fragrance: None detected. Aspect: Facing outward and slightly downward. Height: Approximately 10.5 cm. Width: Approximately 15.8 cm. Quantity of fertile florets per inflorescence: Approximately 40. Quantity of sterile florets per inflorescence: Approximately 240.

*Peduncle.*—Strength: Strong. Shape: Rounded. Length: Approximately 4.2 cm. Diameter: Approximately 3.5 mm. Texture: Matte, moderately covered with thin pubescence having an average length of hairs: 0.5 mm, white in color. Color: 144B.

Floret description:

*General description.*—Type: Single, sterile and fertile. Fertile florets senesce at bud-stage.

*Sterile florets, bud just before opening.*—Shape: Obovate. Length: Approximately 5.0 mm. Diameter: Approximately 4.0 mm. Color: 145B.

*Sterile florets.*—Depth: Approximately 2.0 cm. Diameter: Approximately 3.9 cm. Corolla: 4 petals, often closed forming a central eye. Shape: Rotate, cruciform. Diameter: Approximately 2.0 mm. Calyx: 4 sepals. Shape: Rotate, cruciform. Diameter: Approximately 3.9 cm.

*Petals, sterile florets.*—Shape: Ovate when open, otherwise petals form a center eye of up to 2.0 mm in diameter and lighter than 157D in color. Margin: Entire. Apex: Acute. Base: Cuneate. Length: Approximately 1.5 mm. Width: Approximately 0.5 mm. Texture of upper and lower surfaces: Glabrous, matte. Color of upper surface: NN155B. Color of lower surface: NN155D.

*Sepals, sterile florets.*—Shape: Reniform to near orbicular. Margin: Serrated. Apex: Rounded. Base: Truncate. Length: Approximately 2.3 cm. Width: Approximately 2.9 cm. Texture of upper and lower surfaces: Glabrous, matte. Color of upper surface when first open: 157C to 157D. Color of lower surface when first open: 157C to 157D. Color of upper surface when fully open: NN155D. Color of lower surface when fully open: NN155D.

*Pedicel, sterile florets.*—Strength: Moderately strong. Aspect: Approximately 40° from peduncle axis. Length: Approximately 2.2 cm. Diameter: Approximately 1.5 mm. Texture: Moderately pubescent with appressed hairs having an average length 0.5 mm, white in color. Color: NN155A.

*Fertile florets, bud just before opening.*—Shape: Broadly obovate. Length: Approximately 2.0 mm. Diameter: Approximately 2.0 mm. Color: 145C.

*Fertile florets.*—Fertile florets senesce at bud-stage. Conspicuousness: Inconspicous. Depth: Approximately 4.0 mm. Diameter: Approximately 2.0 mm. Corolla: No corolla and calyx visible, fertile florets dry when developing.

*Pedicel, fertile florets.*—Strength: Strong. Aspect: Erect. Length: Approximately 2.0 mm. Diameter: Approximately 1.0 mm. Texture: Sparsely pubescent with short appressed hairs, green-white in color. Color: 145A to 145B.

*Reproductive organs.*—Observed occasionally in sterile florets only. Fertile florets senesce at bud-stage. Androecium: Stamen quantity: 8 to 10 per floret. Stamen length: Approximately 1.0 mm to 1.5 mm. Filament color: 145B to 145C. Anther shape: Kidney-shaped, basally attached. Anther length: Approximately 1.0 mm. Anther color: 145C to 145D. Pollen amount: None observed. Gynoecium: Pistil quantity: 1 per floret. Pistil length: Approximately 0.5 mm. Stigma shape: Club-shaped. Stigma color: 157A. Style length: Approximately 0.5 mm, two-lobed or three-lobed. Style color: 145D. Ovary length: Approximately 1.5 mm. Ovary texture: Sparsely pubescent with appressed hairs, white in color. Ovary color: 145C.

Seed and fruit production: Neither seed nor fruit production has been observed.

Disease and pest resistance: Resistance to pathogens and pests common to *Hydrangea* has not been observed.

What is claimed is:

1. A new and distinct cultivar of *Hydrangea* plant named 'SAXBRIWHI', substantially as herein illustrated and described.

* * * * *